US 6,180,553 B1

(12) United States Patent
Masi et al.

(10) Patent No.: US 6,180,553 B1
(45) Date of Patent: Jan. 30, 2001

(54) PROCESS AND CATALYST FOR THE HYDROGENATION OF OLEFINICALLY UNSATURATED COMPOUNDS

(75) Inventors: Francesco Masi, S. Angelo Lodigiano; Roberto Santi, Novara; Gianfranco Longhini, Vercelli; Andrea Vallieri, Comacchio, all of (IT)

(73) Assignee: Enichem S.p.A., S. Donato Milanese (IT)

( * ) Notice: Under 35 U.S.C. 154(b), the term of this patent shall be extended for 0 days.

(21) Appl. No.: 09/158,770

(22) Filed: Sep. 23, 1998

(30) Foreign Application Priority Data

Oct. 3, 1997 (IT) ................................. MI97A2249

(51) Int. Cl.$^7$ ........................................ C08F 8/04
(52) U.S. Cl. .................. 502/114; 502/117; 502/152; 502/155; 525/338; 525/339
(58) Field of Search .................. 502/114, 117, 502/152, 155; 525/338, 339

(56) References Cited

U.S. PATENT DOCUMENTS

| 5,169,905 | 12/1992 | Hashiguchi et al. . |
| 5,583,185 | 12/1996 | Parellada Ferrer et al. . |
| 5,739,220 | * 4/1998 | Shamshoum et al. ................. 526/79 |
| 5,753,578 | 5/1998 | Santi et al. . |

FOREIGN PATENT DOCUMENTS

| 0 434 469 | 6/1991 | (EP) . |
| 0 601 953 | 6/1994 | (EP) . |
| 0 841 349 | 5/1998 | (EP) . |

* cited by examiner

Primary Examiner—Bernard Lipman
(74) Attorney, Agent, or Firm—Oblon, Spivak, McClelland, Maier & Neustadt, P.C.

(57) ABSTRACT

Effective catalyst in the selective hydrogenation of olefinic double bonds, comprising the reaction product between:

(A) at least one cyclopentadienyl complex of a transition metal having the following general formula (I):

$$(R)M(R^1)(R^2)(R^3) \qquad (I)$$

wherein:

M is selected from titanium, zirconium and hafnium, preferably titanium;

R is an anion containing an $\eta^5$-cyclopentadienyl ring co-ordinated to M; and each $R^1$, $R^2$ or $R^3$, independently, represents an organic or inorganic group of an anionic nature bound to M, and may, particularly, be hydride, halide, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxyl group, a $C_1$–$C_8$ carboxyl group, a $C_2$–$C_{10}$ dialkylamide group and a $C_4$–$C_{20}$ alkylsilylamide group;

the above compound (I) being solid, supported or dispersed in an inert liquid medium; and (B) at least one organometallic compound of magnesium having the following formula (II):

$$Mg(R^4)_n(R^5)_{(2-n)} \qquad (II)$$

wherein:

$R^4$ is an aliphatic or aromatic hydrocarbon group having from 1 to 20 carbon atoms, $R^5$ is halogen or a group such as $R^4$, and "n" is a decimal number between 0.5 and 2.0, preferably 2.

33 Claims, No Drawings

PROCESS AND CATALYST FOR THE HYDROGENATION OF OLEFINICALLY UNSATURATED COMPOUNDS

The present invention relates to a process and a catalyst for the selective hydrogenation of olefinically unsaturated compounds.

More specifically, the present invention relates to a process for the selective hydrogenation of monomeric or polymeric unsaturated compounds containing at least one olefinic double bond, and a catalyst based on cyclopentadienyl derivatives of a metal of group 4 of the periodic table, which can be used in said process.

The hydrogenation of unsaturated substrates is a technology widely used for obtaining products which can be used in various fields, from the food industry to the field of plastic materials and the like. Several methods are known for the hydrogenation of olefinic double bonds (chemically a reduction by means of hydrogen), most of which use gaseous hydrogen in the presence of a suitable catalyst. The latter normally comprises a transition metal, usually a metal of group 10 of the periodic table, i.e. Ni, Pd or Pt. If these are present as impurities in the hydrogenated substrate, they can cause aging phenomena or toxicological problems in the case of food.

Hydrogenation catalysts based on other transition metals having fewer drawbacks than those listed above, are also known, but these also have a lower catalytic activity.

A particular aspect concerns the hydrogenation of polymeric unsaturated substrates, such as those obtained by the polymerization or copolymerization of conjugated dienes. In the polymeric chain, these polymers have double olefinic bonds which can be used for a possible vulcanization, but make the material unstable, particularly to oxidation, if left unaltered. In addition, with the hydogenation of these polymers, it is possible to obtain materials different from the normal rubbers, which can be used in various industrial fields.

In particular, block copolymers obtained starting from conjugated dienes and from vinyl-substituted aromatic hydrocarbons (especially styrene) can be used, in a non-vulcanized form, as thermoplastic elastomers or as impact-resistant transparent resins or as modifiers of styrene resins and olefinic resins. Owing to the presence of unsaturated double bonds in the polymeric chain, the above block copolymers have poor resistance to oxidation, ozone and atmospheric aging. This is a serious disadvantage for their application.

This lack of stability can be considerably reduced by selectively hydrogenating the olefinic double bonds of the above copolymers.

The known methods for hydrogenating polymers having olefinic double bonds are based on (1) supported heterogeneous catalysts which consist of inert materials (for example silica, alumina, carbon) onto which a metal such as nickel, platinum, palladium or the like is deposited and (2) non-supported catalysts obtained by reacting an organometallic compound of nickel, cobalt, titanium or the like, with a reducing compound such as an organoaluminum or an organolithium.

With respect to supported heterogeneous catalysts (1), non-supported catalysts (2) have the benefit of a greater activity. This is a considerable advantage as it allows blander hydrogenation conditions to be used, with smaller quantities of catalyst.

U.S. Pat. No. 4,501,857 describes a hydrogenation process of non-living polymers carried out in the presence of (A) a bis-(cyclopentadienyl) titanium derivative and (B) at least one organolithium derivative, the molar ratio between lithium atoms and titanium atoms being from 0.1 to 100.

EP-A-434.469 describes a catalytic composition which comprises (a) at least one titanium bis-cyclopentadienyl derivative and (b) at least one compound selected from those having general formula (i) $M^1(AlR^1R^2R^3R^4)$ and (ii) $M^1(MgR^5R^6R^7)$, wherein $M^1$, is selected from lithium, sodium and potassium. Compound (i) can be obtained by the reaction of an organic compound of an alkaline metal with an organometallic derivative of aluminum, whereas compound (ii) can be obtained by the reaction of an organo-alkaline compound with an organo-magnesia derivative.

EP-A-601.953 describes a hydrogenation process carried out in the presence of a catalyst having the general formula $Cp_2Ti(PhO)_2$ or $Cp_2Ti(CH_2PPh_2)2$, wherein Cp is $C_5H_5$.

The above metallocene catalysts of the known art are characterized by the presence of two groups of the cyclopentadienyl type co-ordinated to the titanium atom. In accordance with this it is generally thought that the active catalytic species consists of a stabilized titanium complex having a reduced oxidation state. These catalysts however have catalytic activities and a hardness (average life of the catalyst during the hydrogenation) which are still unsatisfactory for normal industrial processes, in many cases requiring the use of high quantities of metal with the consequent serious contamination of the hydrogenated product. This particularly occurs when the solvent in which the hydrogenation process is carried out is an aliphatic hydrocarbon, such as cyclohexane or heptane, which, on the other hand, is preferable as a solvent compared to aromatic hydrocarbons owing to its greater volatility and lower toxicity.

In addition, it has also been observed that, when the above bis-cyclopentadienyl complexes are used as hydrogenation catalysts, a significant isomerization reaction of the unsaturated hydrocarbons, including the polymers, especially if branched, parallelly takes place, obtaining at times high percentages of product different from that desired. This has the double disadvantage of a decrease in the selectivity and greater difficulty in separating the undesired products.

The Applicant has now found a catalytic composition which can be used in the selective hydrogenation of olefinic double bonds which overcomes the disadvantages mentioned above, as it is simple to prepare and allows significantly higher catalytic activities to be obtained than those achieved so far in the art.

In accordance with this, the present invention relates to a catalytic composition effective in the selective hydrogenation of olefinic double bonds, comprising the reaction product between:

(A) at least one cyclopentadienyl complex of a transition metal having the following general formula (I):

wherein:
M is selected from titanium, zirconium and hafnium, preferably titanium;
R is an anion containing an $\eta^5$-cyclopentadienyl ring co-ordinated to M; and
each $R^1$, $R^2$ or $R^3$, independently, represents an organic or inorganic group of an anionic nature σ-bound to M, and may, particularly, be hydride, halide, a $C_1$–$C_8$ alkyl group, a $C_3$–$C_{12}$ alkylsilyl group, a $C_5$–$C_8$ cycloalkyl group, a $C_6$–$C_{10}$ aryl group, a $C_1$–$C_8$ alkoxyl group, a $C_1$–$C_8$carboxyl group, a $C_2$–$C_{10}$ dialkylamide group and a $C_4$–$C_{20}$ alkylsilylamide group;

the above compound (I) being solid, supported or dispersed in an inert liquid medium; and (B) at least one organometallic compound of magnesium having the following formula (II):

$$Mg(R^4)_n(R^5)_{(2-n)} \qquad (II)$$

wherein:

R$^4$ is an aliphatic or aromatic hydrocarbon group having from 1 to 20 carbon atoms, R$^5$ is halogen or a group such as R$^4$, and "n" is a decimal number between 0.5 and 2.0, preferably 2.

A second aspect of the present invention relates to a process for the preparation of said catalyst, comprising in particular putting the above compounds having formulae (I) and (II) in contact and reacting with each other, preferably in the presence of a liquid medium as diluent.

A further aspect of the present invention relates to a selective hydrogenation process of the olefinic double bonds of a monomeric or polymeric, olefinically unsaturated substrate, comprising putting said substrate in contact and reacting with hydrogen under appropriate conditions of pressure and temperature, in the presence of said catalyst and, preferably, an inert diluent which is normally a solvent of the substrate to be hydrogenated.

As described above, compound (I) in the formation of the catalytic composition of the present invention can be in solid form, possibly in powder form, or it can be supported on an inert solid such as, for example, silica, alumina or silicoaluminates, normally in granular or powder form, or, preferably, it can be dispersed in an inert liquid medium, either as a multiphase system, when compound (I) is insoluble in said liquid, or as a homogeneous solution when the liquid is a solvent of the compound having formula (I).

The diluent can also be introduced into the reaction container before charging the reagents. It must be inert towards the compounds having formulae (I) and (II). The diluent is preferably selected from aliphatic or cycloaliphatic saturated hydrocarbons having from 3 to 15 carbon atoms and relative mixtures. Typical examples of these diluents are propane, butane, n-hexane, n-pentane, iso-pentane, n-heptane, octanes, decanes, cyclopentane, variously alkylated cyclopentanes, cyclohexane, variously alkylated cyclohexanes. The preferred diluent is cyclohexane.

Compounds having formula (I) which form component (A) of the catalyst according to the present invention are monocyclopentadienyl complexes of titanium, zirconium or hafnium, i.e. compounds containing only one η$^5$-cyclopentadienyl anion co-ordinated to an atom of these metals. Compounds of this type, as well as methods for their preparation, are known and defined, more specifically, as compounds in which the metal M is co-ordinated by an R derivative anionic group, formally by the extraction of an H$^+$ ion from the cyclopentadienyl ring, from a cyclopentadienyl, indene or fluorene molecule, as such or substituted on one or more carbon atoms of the molecular skeleton (included or not included in the cyclo-pentadienyl ring). Normal substituents are halogens, particularly chlorine or fluorine, C$_1$–C$_8$ alkyl or silylalkyl groups, or C$_6$–C$_{10}$ aryl or aryloxy groups, or C$_1$–C$_8$ alkoxyl groups, optionally halogenated, or condensed with one or more other aromatic or aliphatic rings as in the case, for example, of 4,5-benzoindenyl. Typical but non-limiting examples of this R group are cyclopentadienyl, indenyl, 4,5,6,7-tetrahydroindenyl groups and the corresponding methylsubstituted groups, particularly pentamethylcyclopentadienyl.

The substituents R$^1$, R$^2$ and R$^3$ in the complex having formula 1 can be formally identified as inorganic or organic anions, which are bound to the metal M with an at least partially covalent bond of the "σ" type, as is already known to chemical experts of transition metals. These groups are preferably selected, independently of each other, from halides, carboxylates, amides, alcoholates and β-diketonates, owing to their availability and stability. More preferably, the three groups R$^1$, R$^2$ and R$^3$ are the same and are selected, for example, from chloride, bromide, acetate, trifluoroacetate, versatate, butylate and propylate, dimethylamide, diethylamide. In addition, according to the present invention, two groups selected from R$^1$, R$^2$ and R$^3$, or also all three groups, can be joined to each other to form a single di- or tri-anion bound to the metal M forming at least one cyclic structure comprising this. Finally, comprised in the scope of formula (I) are also complexes in which one of the groups R$^1$, R$^2$ or R$^3$ is a group bound to the metal M by means of a heteroatom selected from O, S, N, P, and at the same time bound to the cyclopentadienyl group R by means of a covalent bridge which can also comprise divalent groups of the alkylene, arylene or silylene type. Typical examples of these bridge-complexes and examples of synthetic methods are provided, for example in European patent application 416.815. Other synthetic methods of complexes having formula (I) are described in specialized literature of the field.

Depending on the nature of groups R$^1$, R$^2$ and R$^3$, the solubility of the complex in the reaction diluent may vary considerably. Organic groups such as alcoholates or carboxylates increase the solubility of these complexes in aliphatic hydrocarbons. It has been observed however that in certain cases, at the end of the reaction of components (A) and (B), or, in any case, after contact of the catalyst with hydrogen, the active principle which is formed is of a solid nature, in the form of a fine particulate in suspension in the inert diluent which also forms the liquid medium in which the hydrogenation process preferably takes place.

Typical but non-limiting examples of compounds having formula (I) which can be used for the formation of the catalytic composition of the present invention are specified below:

(η$^5$-C$_5$H$_5$)TiCl$_3$, (η$^5$-THInd)TiCl$_3$ (η$^5$-Ind)Ti(NMe$_2$)$_3$, [Me$_2$Si(η$^5$-Ind) (CH$_2$CH$_2$O)]TiCl$_2$ (η$^5$-Flu)TiCl$_3$, [Me$_2$Si(η$^5$-C$_5$Me$_4$)(NBu$_t$)]TiCl$_2$ (η$^5$-C$_5$Me$_5$)TiCl$_3$, (η$^5$-C$_5$Me$_5$)TiMeCl$_2$ (η$^5$-C$_5$H$_5$)TiCl$_2$Me), (η$^5$-THInd)Ti(OMe)$_3$ (η$^5$-Ind)Ti(OMe)$_3$, (η$^5$-Ind)TiCl$_3$ (η$^5$-C$_5$H$_5$)TiCl$_2$Ph, [Ph$_2$Si (η$^5$-Ind)(CH$_2$COO)]TiCl$_2$ (η$^5$-C$_5$Me$_5$)TiCl$_2$Ph, [η$^5$-(1,2-(Me)$_2$THInd)]TiCl$_3$ (η$^5$-Flu)Ti(OBu)$_3$, [η$^5$-(1,2-(Me)$_2$Ind)]TiCl$_3$ (η$^5$-THInd)Ti(OBu)$_3$, [o-xen(η$^5$-Ind)(CH$_2$O]TiCl$_2$ (η$^5$-C$_5$Me$_5$)Ti(OBu)$_3$, (η$^5$-C$_5$H$_5$)TiCl(OCOPh)$_2$ (η$^5$-C$_5$Me$_5$)TiPh(Cl)$_2$, (η$^5$-C$_5$Me$_5$)Ti[OCO(CH$_2$)$_m$Me]$_3$ (η$^5$-C$_5$Me$_5$)Ti(OPh)$_3$, (η$^5$-C$_5$H$_5$)Ti[OCO(CH$_2$)$_m$Me]$_3$ (η$^5$-Ind)Ti(OCOCF$_3$)$_3$, (η$^5$-C$_5$Me$_5$)Ti(OCOMe)$_3$ (η$^5$-Ind)Ti(OCOMe)$_3$, (η$^5$-C$_5$H$_5$)Ti(Oxacalix-3-arene)

(η$^5$-C$_5$H$_5$)Ti(OCOMe)$_3$, (η$^5$-Flu)Ti[OCO(CH$_2$)$_m$Me]$_3$ (η$^5$-THInd)Ti(OCOCF$_3$)$_3$, (η$^5$-C$_5$H$_5$)TiCl$_{1.5}$(OCOCHEt(CH$_2$)$_3$Me]$_{1.5}$ (η$^5$-THInd)Ti(OCOMe)$_3$, (η$^5$-C$_5$Me$_5$)Ti(OCOCHEt(CH$_2$)$_3$Me]$_3$

[η$^5$-(1-Me$_3$Si)Ind]TiCl$_3$, [η$^5$-(1,3-(CF$_3$)$_2$C$_5$H$_3$)]Ti(OCOMe)$_3$ (η$^5$-C$_5$Me$_5$)Ti(OCOCF$_3$)$_3$.

The following abbreviations were used in the above formulae: Me=methyl, Bu=butyl, Ind=indenyl, THInd=4,5, 6,7-tetrahydro-indenyl, Flu=fluorenyl, Ph=phenyl, Et=ethyl. The subscript "m" where it appears in the formulae indicates an integer between 1 and 16.

According to the present invention, the above complexes having formula (I) can be used in pure form or supported on an inert solid medium consisting, for example, of a porous inorganic solid such as silica, alumina, silicoaluminates, possibly dehydrated and activated according to the methods known in the art, or consisting of a polymeric organic solid such as polystyrene, so as to obtain, at the end of the preparation, a supported catalytic composition.

According to a particular aspect of the present invention, component (A) of the present catalytic composition is obtained by the contact of a complex having formula (I) wherein $R^1$, $R^2$ and $R^3$ are all different from alkyl or aryl, with an organic compound of lithium, preferably a lithium alkyl or a lithium aryl. Preferred organic compounds of lithium are lithium methyl, lithium phenyl and lithium benzyl, particularly lithium phenyl. Other lithium aryls in which the phenyl ring is substituted by $C_1$–$C_6$ aliphatic groups can also be advantageously used to obtain component (A). Preferred complexes having formula (I) in this particular aspect are those in which groups $R^1$, $R^2$ and $R^3$ are chloride. The organic compound of lithium and the complex having formula (I) are put in contact in such proportions that the atomic ratio Li/M is between 1 and 8, preferably between 1.5 and 4. The reaction preferably takes place in an inert liquid medium such as, for example, an aliphatic hydrocarbon, at temperatures not higher than 100° C., preferably between 10 and 40° C., for a period between 5 and 30 minutes.

The organo-magnesium derivatives having formula (II) are typically selected from alkylmagnesium halides, normally known as Grignard compounds, and magnesium dialkyls. Both groups of compounds are known and numerous methods have been published for their preparation. Many of these magnesium compounds are commercial products, usually in the form of a solution of an inert aliphatic hydrocarbon. Among organometallic compounds of magnesium suitable for the preparation of the catalytic composition of the present invention, magnesium dialkyls are preferred, i.e. compounds having formula (II) wherein both $R^4$ and $R^5$ are selected from linear or branched $C_1$–$C_{16}$, preferably $C_1$–$C_{10}$ alkyls. Typical examples of magnesium dialkyls are magnesium di-n-butyl, magnesium di-isobutyl, magnesium di-isopropyl, magnesium butyl-isobutyl, magnesium di-cyclohexyl, magnesium butyl-octyl and relative mixtures.

With respect to the magnesium compound having formula (II), which forms component (B) of the present catalytic composition, this is added to the reaction environment preferably in the form of a solution in an aliphatic or cycloaliphatic hydrocarbon solvent, such as for example, cyclohexane.

According to a preferred embodiment of the present invention, the reaction between components (A) and (B) for the formation of the catalytic composition, takes place in the presence of a modifier (C) consisting of a polar aprotic organic compound, preferably having from 2 to 30 carbon atoms, which has an activating and stabilizing function of the catalytic site. Compounds of this type are also known as Lewis bases, and comprise different groups of aliphatic or aromatic organic compounds containing at least one heteroatom selected from N, P, O, S, As and Se.

Preferred modifiers (M) are ethers, such as for example, dimethylether, diethylether, di-n-propylether, diisopropylether, di-n-butylether, di-sec-butylether, di-t-butylether, diphenylether, methylethylether, ethylbutylether, butylvinylether, anisol, ethylphenyl ether, ethyleneglycoldimethylether, ethyleneglycoldiethylether, ethyleneglycol dibutylether, diethyleneglycoldimethylether, diethyleneglycoldiethylether, diethyleneglycoldibutylether, polyethyleneglycoldimethylethers, polyethyleneglycoldiethylether, polyethyleneglycoldibutylether, tetrahydrofuran, alpha-methoxy-tetrahydrofuran, ethers of 2-hydroxymethyl-tetrahydrofuran, pyrane, dioxane, di(tetrahydrofuran) propane. In the above list of ethers, the term "butyl" refers to all possible isomers, i.e. n-butyl, iso-butyl and terbutyl. Particularly preferred are cyclic ethers, such as tetrahydrofuran or pyrane and di- or polyethers, such as $C_1$–$C_{20}$ ethers of ethylene glycol and diethyleneglycol, even more preferred are $C_1$–$C_4$ ethers of glycol and ethylene diglycol.

In the preferred embodiment, the molar ratio between the magnesium compound having formula (II) and the monocyclopentadienyl derivative (I) is between 1:1 and 20:1, more preferably between 2:1 and 10:1.

The molar ratio between the metal M and the modifier (C), when the latter is present, is preferably higher than 0.001. This ratio is more preferably between 0.003 and 100; for ratio values higher than 100, the possible advantageous effect of the co-ordinating compound is no longer significant. Particularly preferred ratios are between 0.01 and 10.0.

The modifier (C) can be added as such or, preferably, in an aliphatic or cycloaliphatic hydrocarbon solution, more preferably mixed with component (A). In the latter case, if component (A) is obtained from the reaction between a compound having formula (I), preferably with M=Ti, and a lithium alkyl or aryl, the modifier (C) is preferably introduced into the catalytic composition together with the lithium compound. Alternatively, the modifier (C) can be introduced into the reaction environment together with the compound having formula (II), or separately diluted in the solvent used for the hydrogenation process.

According to a particular aspect of the present invention, the above components (A), (B) and, optionally, (C), are put in contact and reacted with each other in the presence of an aromatic hydrocarbon, normally mixed with the reaction diluent. This aromatic hydrocarbon is preferably present in such quantities as to have a molar ratio with respect to the metal M of component (A) ranging from 10 to 1000, and is selected from compounds having from 6 to 20 carbon atoms, such as, for example, toluene, xylenes, ethylbenzene, 6-dodecylbenzene, naphthalene, tetralin, biphenyl, indane and their mixtures.

Under the above conditions, at the end of the contact between the reagents, a finely subdivided, dark-coloured, from brown to purplish-brown, suspension is preferably formed. Depending on the nature of the components and reactions conditions, a homogeneous solution may initally be formed which subsequently becomes a suspension.

As far as the temperature and reaction times between (A), (B) and, optionally, (C), are concerned, these are not particularly critical and are within wide limits, to obtain the catalyst of the present invention. It is preferable however for the temperature to be between 0° C. and 100° C., more preferably between 20° C. and 70° C. The contact time between the reagents ranges from a few minutes to several hours, usually more than 3 minutes, even more preferably up to 2 hours.

The preparation of the catalyst must be carried out in an inert atmosphere. The term "inert atmosphere" refers to an atmosphere of gases which do not react with any of the species present in the reaction environment. Typical examples of these gases are helium, neon, argon, and relative mixtures. Alternatively hydrogen can also be used. Air and oxygen are not appropriate because they oxidate or decompose the hydrogenation catalyst making it inactive. Nitrogen is also not appropriate as it reacts with the activated form of the catalyst, destroying it.

According to another embodiment of the present invention, the catalytic composition in question can be prepared in the presence of the unsaturated compound which is to be hydrogenated. The latter can form the diluent itself in which the preparation of the catalyst is effected, or it can be mixed with an inert diluent of the type described above. In particular, especially in the case of non-polymeric unsaturated compounds, the compound to be hydrogenated can be added entirely or partially to component (A) before the reaction with component (B) and possible component (C). Alternatively, the unsaturated compound is added after contact between (A) and (B), but before introducing the hydrogen.

The present invention also relates to a process for the hydrogenation of olefinic double bonds present both in compounds having a low molecular weight, and in unsaturated oligomers or polymers and copolymers, preferably obtained by the (co)polymerization of conjugated dienes, which comprises putting the substrate to be hydrogenated in contact with hydrogen in an inert solvent, in the presence of the catalytic composition according to claim 1, for a period sufficient to obtain a selective hydrogenation of at least 50%, preferably at least 90% of the olefinic double bonds.

Non-polymeric substrates which can be hydrogenated according to the process of the present invention consist of the usual aliphatic and aromatic olefins having from 2 to 30, preferably from 4 to 25, carbon atoms, such as ethylene, propylene, butenes, octenes, cyclohexene, cyclohexadiene, undecene, cyclododecatetraene, norbornene, styrene (selective hydrogenation to ethylbenzene), divinylbenzenes, conjugated dienes such as butadiene, isoprene, chloroprene, non-conjugated dienes such as ethylidenenorbornadiene, 1,4-hexadiene and the like, acetylene derivatives such as acetylene, 2-butane, 1-hexyne. Equally suitable as substrates are also olefins and styrene derivatives comprising heteroatoms such as, for example, halogens, especially chlorine and fluorine, silicon, boron, sulfur, oxygen. Other non-polymeric unsaturated substrates consist, for example, of esters of unsaturated fatty acids, such as linoleic or ricinoleic acids, esters of unsaturated acids with a short chain such as, for example, acrylic, methacrylic, maleic or fumaric acid, vinyl esters of aliphatic or aromatic acids, organic imines (also commonly called Schiff bases).

The hydrogenation of these substrates can be carried out in an inert diluent medium, or also on the compound to be hydrogenated as such. The process is carried out in suitable reactors, under hydrogen pressure usually ranging from 0.5 to 10 MPa, preferably at temperatures ranging from 40 to 100° C. and for times varying from 10 minutes to several hours, depending on the substrate to be hydrogenated and the hydrogenation degree desired. Blander conditions can be used, for example, if a primary double bond is to be hydrogenated, leaving a secondary one intact in a non-conjugated diene.

With respect to the hydrogenation reaction of (co) polymers, this is carried out under normal conditions (temperature, hydrogen pressure, solvent) well-known in the art. It is possible to use, for example, temperatures ranging from 40 to 150° C., preferably from 70 to 130° C., pressures ranging from 0.1 to 10, preferably from 0.2 to 5, MPa, the solvents of the (co)polymers preferably consisting of aliphatic or cycloaliphatic, saturated hydrocarbons, having from 6 to 15 carbon atoms and relative mixtures. It is evident that higher temperatures and pressures accelerate the hydrogenation rate.

According to an embodiment, the solution of the polymer to be hydrogenated is charged, under a hydrogen atmosphere, into the hydrogenation reactor followed by the catalyst dispersion. The whole mixture is then pressurized with hydrogen and brought to the desired temperature. When the hydrogenation is complete, the hydrogenated polymer is recovered according to the known techniques which comprise, for example, direct distillation of the solvent, or coagulation of the polymer with a non-solvent, its recovery and subsequent drying.

The catalytic compositions which can be obtained with the process of the present invention are also active in the hydrogenation process in very low quantities, indicatively up to 10 ppm of M with respect to the substrate to be subjected to hydrogenation, with a ratio between moles of metal M and olefinic double bonds of up to 1:60000. This is a definite advantage with respect to the catalysts of the known art.

The (co)polymers of conjugated dienes mentioned above include homopolymers of conjugated dienes, interpolymers of different conjugated dienes and copolymers obtained by copolymerizing at least one conjugated diene with at least one olefin copolymerizable with the above conjugated diene.

Typical examples of conjugated dienes are 1,3-butadiene, isoprene, 2,3-dimethyl-1,3-butadiene, 1,3-pentadiene, 2-methyl-1,3-pentadiene, 1,3-hexadiene, 4,5-diethyl-1,3-octadiene and 3-butyl-1,3-octadiene. Isoprene and 1,3-butadiene, more preferably 1,3-butadiene are particularly useful as intermediates for the production of elastomers having excellent physico-chemical properties. Typical examples are therefore polybutadiene, polyisoprene and butadiene/isoprene copolymers.

Olefinic monomers which can be used in the copolymerization together with the dienes listed above, are all unsaturated monomers copolymerizable with the above conjugated dienes, particularly vinyl substituted aromatic hydrocarbons. Among these styrene, t-butyl styrene, alpha-methyl-styrene, o-methyl styrene, p-methyl styrene, vinyl naphthalene are particularly suitable. In particular the most useful vinyl aromatic compound is styrene.

Typical examples of block copolymers which can be used as substrates in the hydrogenation process described above are those having general formula (B-T-A-B)$_m$X and (A-T-B)$_m$X, wherein B are polydiene blocks, the same or different from each other, A is a polyvinylaromatic block, T is a statistic copolymeric segment consisting of diene and vinylaromatic monomeric units, X is a coupling radical with a valence "m", "m" is an integer from 1 to 20, the content of segment T preferably being up to 40% by weight. When "m" is equal to 1, X is the residue of a quenching agent, for example -Si-(CH$_3$)$_3$ when monochlorotrimethylsilane is used; when "m" is equal to or higher than 2, X is the residue of a coupling agent, such as for example =Si(CH$_3$)$_2$ in the case of dimethyldichlorosilane, ≡Si(CH$_3$) in the case of methyltrichlorosilane and =Si= in the case of silicon tetrachloride.

In the above block copolymers, the content of vinylsubstituted aromatic hydrocarbons is from 5 to 95%, preferably between 10 and 60%. In the above copolymers, the content of 1,2 or 3,4 units of polydiene phase can vary from 10 to 80%, preferably from 30 to 60%, depending on the quantity and type of vinylpromoter agent used in the synthesis of the starting unsaturated polymer.

As well as the styrene-diene block copolymers mentioned above, it is possible to hydrogenate with the process of the present invention random copolymers with a linear or branched structure having monomers statistically distributed in the polymeric chain and quantities of 1,2 or 3,4 units varying from 10 to 80% by weight.

The (co)polymers which can be used in the hydrogenation process of the present invention do not have a particular molecular weight. However they generally have a number average molecular weight ranging from 1000 to about a million.

The (co)polymers which can be used in the hydrogenation process of the present invention can be produced according to the known (co)polymerization methods a description of which can be found in the vast specialized literature in the field.

Using the catalytic composition of the present invention, it is possible to carry out the hydrogenation of polymeric substrates with a surprisingly low quantity of metal (especially titanium) with respect to the substrate mass, in a diluent consisting of an aliphatic hydrocarbon which does not allow the usual hydrogenation processes to be carried out in homogeneous phase with traditional catalysts.

The present invention is further illustrated by the following examples which however in no way restrict the overall scope of the invention itself.

EXAMPLE 1

Hydrogenation of 1-octene With $Cp^*Ti(OCOCF_3)_3$ 0.12 mmoles of ($n^5$-pentamethylcyclopentadienyl) titanium tris(trifluoroacetate) $[Cp^*Ti(OCOCF_3)_3]$(obtained according to the method described in Italian patent application MI97 A 00432), 20 ml of anhydrous cyclohexane, 0.03 ml of a solution of n-dibutylglima 0.45 M in anhydrous cyclohexane and 0.54 ml of 1 molar $Mg(butyl)_2$ in n-heptane (Aldrich commercial product; atomic ratio Mg/Ti=4.5), are charged into a tailed test-tube equipped with a magnetic stirrer, in an atmosphere of argon. The mixture is left under stirring for 2 hours at room temperature (the solution takes on an extremely dark colouring). 18.8 ml of 1-octene (distilled and maintained on molecular sieves) are added. The mixture thus obtained is siphoned in an autoclave previously maintained under argon. It is then pressurized with 5.06 MPa (50 atms) of hydrogen and the temperature is brought to 60° C. by heating with an oil bath (external temperature). The hydrogenation process thus activated is prolonged for 90 minutes, the reaction mixture being maintained under stirring and continuously feeding hydrogen to keep the pressure at a constant value. At the end the stirring is stopped and the mixture is left to cool to room temperature. About 18 ml of octane are obtained by distillation (GC, GC-mass and NMR analyses), with a substantially complete hydrogenation conversion.

EXAMPLE 2

Hydrogenation of trans-4-methyl-2-pentene With $Cp^*Ti(OCOCF_3)_3$ 0.06 mmoles of $Cp^*Ti(OCOCF_3)_3$ complex, 10 ml of anhydrous cyclohexane, 0.015 ml of a solution of n-dibutylglima 0.45 M in anhydrous cyclohexane and 0.27 ml of 1 molar $Mg(butyl)_2$ in n-heptane (atomic ratio Mg/Ti=4.5), are charged into a tailed test-tube equipped with a magnetic stirrer, in an atmosphere of argon. The mixture is left under stirring for 2 hours at room temperature (the solution takes on an extremely dark colouring). 30 mmoles (3.5 ml) of trans-4-methyl-2-pentene (distilled and maintained on molecular sieves) are added. At this point the solution is siphoned in an autoclave previously maintained under argon. It is then pressurized with 2.53 MPa (25 ate) of hydrogen and the same procedure is carried out as described in example 1 above. The reaction product is filtered and gaschromatographic analysis is carried out on the remaining solution. A mixture of 2-methylpentane/trans-4-methyl-2-pentene is obtained (weight ratio 7/1). The results and process conditions are summarized in table 1 below.

EXAMPLE 3

Hydrogenation of 1-octene With $Cp^*TiCl_3$ 0.12 mmoles of ($\eta^5$-pentamethylcyclopentadienyl) titanium trichloride ($Cp^*TiCl_3$; Aldrich commercial product), 20 ml of anhydrous cyclohexane, 0.03 ml of a solution of n-dibutylglima 0.45 M in anhydrous cyclohexane and 0.54 ml of $Mg(butyl)_2$ 1M in n-heptane (atomic ratio Mg/Ti=4.5), are charged into a tailed test-tube equipped with a magnetic stirrer, in an atmosphere of argon. The mixture is left under stirring for 2 hours at room temperature (the solution takes on an extremely dark colouring). 18.8 ml of 1-octene (distilled and maintained on molecular sieves; molar ratio 1-octene/Ti=1000) are added. At this point the solution is siphoned in an autoclave previously maintained under argon and the same procedure is carried out as described in example 1 above. At the end it is cooled to room temperature. About 18 ml of octane are obtained by distillation (GC, mass GC and NMR analyses). The results and process conditions are summarized in table 1 below.

EXAMPLE 4

Reduction With $Cp^*TiCl_3$, of 1-octene 0.12 mmoles of $Cp^*TiCl_3$, 20 ml of anhydrous cyclohexane, 0.03 ml of a solution of n-dibutylglima 0.45 M in anhydrous cyclohexane and 0.54 ml of 1 molar Mg(butyl)$_2$ in n-heptane (atomic ratio Mg/Ti=4.5), are charged into a tailed test-tube equipped with a magnetic stirrer, in an atmosphere of argon. The mixture is left under stirring for 2 hours at room temperature (the solution takes on an extremely dark colouring). 5 ml of this solution are removed and 18.8 ml of 1-octene (distilled and maintained on molecular sieves; molar ratio 1-octene/Ti=4000) are added. At this point the solution is siphoned in an autoclave previously maintained under argon and the same procedure is carried out as described in example 1 above. At the end it is cooled to room temperature. About 18 ml of octane are obtained by distillation (GC and NMR analyses). The results and process conditions are summarized in table 1 below.

EXAMPLE 5

Hydrogenation With $CpTiCl_3$ of 1-octene 0.12 mmoles of ($\eta^5$-cyclopentadienyl)titanium trichloride ($CpTiCl_3$; Aldrich commercial product), 20 ml of anhydrous cyclohexane, 0.03 ml of a solution of n-dibutylglima 0.45 M in anhydrous cyclohexane and 0.54 ml of 1 molar $Mg(butyl)_2$ in n-heptane (atomic ratio Mg/Ti=4.5), are charged into a tailed test-tube equipped with a magnetic stirrer, in an atmosphere of argon. The mixture is left under stirring for 20 hours at room temperature (the solution takes on an extremely dark colouring). 18.8 ml of 1-octene (distilled and maintained on molecular sieves) are added. At this point the solution is siphoned in an autoclave previously maintained under argon and the same procedure is carried out as described in example 1 above. At the end it is cooled to room temperature. About 18 ml of octane and 0.4 ml of 2-octene are obtained by distillation (GC, mass GC and NMR analyses). The results and process conditions are summarized in table 1 below.

EXAMPLE 6 (COMPARATIVE)

Hydrogenation With $Cp_2TiCl_2$ of 1-octene 0.12 mmoles of bis-($\eta^5$-cyclopentadienyl)titanium dichloride ($Cp_2TiCl_2$; Aldrich commercial product), 20 ml of anhydrous cyclohexane, 0.03 ml of a solution of n-dibutylglima 0.45 M in anhydrous cyclohexane and 0.54 ml of 1 molar $Mg(butyl)_2$ in n-heptane (atomic ratio Mg/Ti= 4.5), are charged into a tailed test-tube equipped with a magnetic stirrer, in an atmosphere of argon. The mixture is left under stirring for 20 hours at room temperature. 18.8 ml of 1-octene (distilled and maintained on molecular sieves) are added. At this point the solution is siphoned in an autoclave previously maintained under argon and the same procedure is carried out as described in example 1 above. At the end it is cooled to room temperature. About 14 ml of octane and 4 ml of 2-octene are obtained by distillation (GC, mass GC and NMR analyses). The results and process conditions are summarized in table 1 below.

whole duration of the hydrogenation process by the continuous feeding of additional hydrogen to substitute that used up by the reaction. After 60 minutes of reaction the temperature in the reactor is brought to 90° C. The progression of the reaction is controlled by measuring the gradual decrease in olefinic unsaturations of samples taken from the reactor. The results obtained are indicated in Table 2.

EXAMPLE 8 (COMPARATIVE)

A hydrogenation reaction is carried out using the same procedure, catalyst and ratios between the reagents as in example 7 above, with the only difference that, during the preparation of the reactor, magnesium dibutyl is not added after the introduction of the SBS polymeric solution. The results are shown in Table 2.

EXAMPLE 9

A hydrogenation reaction is carried out with the same procedure, catalyst and ratios between the reagents as in example 7 above, with the only difference that, during the hydrogenation, the temperature is brought from 70 to 90° C., 30 minutes after the beginning of the reaction, instead of 60 minutes after. The results are indicated in Table 2.

TABLE 1

Olefin hydrogenation (T = 60° C., time = 90 min., modifier n-dibutylglima)

| Example | Complex | Molar ratio double bonds/Ti | Molar ratio Mg/Ti | $P_{hydrog.}$ (MPa) | Olefin | Compound % convers. |
|---|---|---|---|---|---|---|
| 1 | [Cp*Ti(OCOCF$_3$)$_3$] | 1000 | 4,5 | 5,06 | 1-octene | 100, n-octane |
| 2 | [Cp*Ti(OCOCF$_3$)$_3$] | 500 | 4,5 | 2,53 | 2-methylpent-1-ene | 87.5, 2-methylpentane |
| 3 | [CP*TiCl$_3$] | 1000 | 4,5 | 5,06 | 1-octene | 100, n-octane |
| 4 | [CP*TiCl$_3$] | 4000 | 4,5 | 5,06 | 1-octene | 100, n-octane |
| 5 | [CpTiCl$_3$] | 1000 | 4,5 | 5,06 | 1-octene | 98.2, n-octane |
| 6 | [Cp$_2$TiCl$_2$] | 1000 | 4,5 | 5,06 | 1-octene | 78, n-octane |

EXAMPLE 7

A) Preparation of the Catalytic Composition

The following products are charged in order into a 100 ml Schlenk tube, under an argon atmosphere: 0.055 g (0.25 mmoles) of cyclopentadienyltitanium trichloride (CpTiCl$_3$), 20 ml of cyclohexane and 0.28 ml (0.50 mmoles) of a solution of phenyllithium 1.8 M in a mixture of cyclohexane/ethyl ether having a composition of 70/30, so as to have an atomic ratio Li/Ti of 2. This mixture is left under stirring in an argon atmosphere for 15 minutes at a temperature ranging from 20 to 30° C.

B) Hydrogenation Reaction 800 g of polymeric solution of the type SBS at 12.5% by weight (having a vinyl content of 45%, a percentage composition of styrene/butadiene of 30.3/69.7 by weight and a molecular weight of 56000) are charged into a 2 liter Buchi type steel reactor, 2 ml of magnesium dibutyl 1 M in a solution of n-heptane are then added and the system is thermostat-regulated at 70° C. under stirring in a hydrogen atmosphere. The catalytic composition prepared as under point (A) above is added to the reactor thus prepared, so as to obtain a quantity of Ti equal to 120 ppm with respect to the dry polymer, with a ratio (olefinic double bonds)/(Ti moles) equal to 5160. The hydrogen pressure in the reactor is brought to 2.4 MPa and maintained at this value for the

EXAMPLE 10

A) Preparation of the Catalytic Composition

The following products are charged into a 100 ml Schlenk tube, under an argon atmosphere: 20 ml of cyclohexane, then 0.74 ml (0.74 mmoles) of magnesium dibutyl 1 M in a solution of n-heptane, then 2.7 ml of a solution of cyclopentadienyltitanium trichloride (CpTiCl$_3$) in THF, having a concentration of 10 g/l of complex (0.123 mmoles) are added, so as to have a molar ratio Mg/Ti of about 6. This mixture is left under stirring in an argon atmosphere for 30 minutes, at a temperature ranging from 20 to 30° C.

B) Hydrogenation Reaction 400 g of polymeric solution of the type SBS at 12.3% by weight (having 46.9% of vinyl, a percentage composition of styrene/butadiene of 29.6/70.4 and MW of 48.600) are charged into a 1 liter Buchi type steel reactor and the system is thermostat-regulated at 130° C. under stirring in a hydrogen atmosphere. The catalytic composition prepared as under point (A) above is added to the reactor thus prepared, so as to obtain a quantity of Ti equal to 120 ppm with respect to the dry polymer, with a ratio (olefinic double bonds)/(Ti moles) equal to 5160. The hydrogen pressure in the reactor is rapidly brought to 2.4 MPa and maintained at this value for the whole duration of the hydrogenation process by the continuous feeding of additional hydrogen to substitute that used up by the reaction. The temperature is maintained at 130° C. and the reaction is continued until the complete hydrogenation of all the olefinic unsaturations of the polymer. The results obtained are indicated in Table 2.

EXAMPLE 11

A) Preparation of the Catalytic Composition

The following products are charged into a 100 ml Schlenk tube, under an argon atmosphere: 20 ml of cyclohexane, then 0.14 ml of phenyl lithium 1.8 M in a solution of cyclohexane/ethyl ether having a percentage composition of 70/30 (0.246 mmoles) so as to have a molar ratio Li/Ti equal to 2. 2.7 ml of a 10 g/l solution in THF of cyclopentadienyl titanium trichloride (CpTiCl$_3$), (0.123 mmoles) are then added. The mixture is left under stirring for about 15 minutes at a temperature ranging from 20 to 30° C., then 0.25 ml (0.25 mmoles) of magnesium dibutyl 1 M in a solution of n-heptane are then added. The reaction mixture thus prepared is left under stirring for a further 15 minutes.

B) Hydrogenation Reaction

A hydrogenation test is carried out on the same polymeric substrate and with the same procedure described in example 10B above, with the difference that in this case the catalytic composition prepared as indicated above, is used. The hydrogenation is therefore carried out with a quantity of titanium equal to 120 ppm with respect to the dry polymer, and with a ratio (olefinic bonds)/(moles of titanium) equal to 5160. The results obtained are indicated in Table 2.

Numerous variations and modifications of the above process are obviously possible, depending on the projects and techniques available in the field, which however are entirely included in the scope of the present invention.

(B) at least one organometallic compound of magnesium having the following formula (II):

$$Mg(R^4)_n(R^5)_{(2-n)} \qquad (II)$$

wherein:
R$^4$ is an aliphatic or aromatic hydrocarbon group having from 1 to 20 carbon atoms,
R$^5$ is halogen or a group such as R$^4$, and
"n" is a decimal number between 0.5 and 2.0.

2. The composition according to claim 1, wherein each R$^1$, R$^2$ or R$^3$, is independently selected from the group consisting of hydride, halide, a C$_1$–C$_8$ alkyl group, a C$_3$–C$_{12}$ alkylsilyl group, a C$_5$–C$_8$ cycloalkyl group, a C$_6$–C$_{10}$ aryl group, a C$_1$–C$_8$ alkoxyl group, a C$_1$–C$_8$ carboxyl group, a C$_2$–C$_{10}$ dialkylamide group and a C$_4$–C$_{20}$ alkylsilylamide group.

3. The composition according to claim 1 or 2, wherein, in the compound having formula (II), R$^4$ and R$^5$ are both, independently, linear or branched, aliphatic hydrocarbon groups, having from 2 to 10 carbon atoms.

4. The composition according to claim 1, wherein the index "n" in formula (II) of claim 1 is equal to 2.

5. The composition according to any of the previous claims, wherein the compound having formula (I) in said component (A) is dispersed in an inert liquid medium selected from the group consisting of aliphatic or cycloaliphatic saturated hydrocarbons and relative mixtures.

6. The composition according to any of the previous claims, wherein the substituents R$^1$, R$^2$ and R$^3$ in said compound having formula (I) are independently selected from the group consisting of halides, carboxylates, amides, alcoholates and β-diketonates.

7. The composition according to claim 6, wherein the groups R$^1$, R$^2$ and R$^3$ in the compound having formula (I)

TABLE 2

Hydrogenation of unsaturated polymeric substrates in cyclohexane

| | | Temperature | | Conversion (% hydrogenated double bonds) | | |
|---|---|---|---|---|---|---|
| Example | Catalyst | (° C.) | Substrate | 60 min. | 120 min. | 150 min. |
| 7 | CpTiCl$_3$ + LiPh + Mg(Bu)$_2$ | 70–90 | SBS-1 | 59,2 | 89,8 | 98,6 |
| 8(comp.) | CpTiCl$_3$ + LiPh | 70–90 | SBS-1 | 9,4 | 10,6 | 11,2 |
| 9 | CpTiCl$_3$ + LiPh + Mg(Bu)$_2$ | 70–90 | SBS-1 | 75,3 | 88,1 | 93,1 |
| 10 | CpTiCl$_3$ + THF + Mg(Bu)$_2$ | 130 | SBS-2 | 95,5 | 98,8 | — |
| 11 | CpTiCl$_3$ + LiPh + THF + Mg(Bu)$_2$ | 130 | SBS-2 | 95,9 | 99.0 | — |

SBS-1: vinyl content = 45%, styrene/butadiene = 30.3/69.7 by weight, molecular weight = 56000
SBS-2: vinyl content = 46.9%, styrene/butadiene = 29.6/70.4 by weight, molecular weight = 48600

What is claimed is:

1. A catalytic composition effective in the selective hydrogenation of olefinic double bonds, comprising the reaction product between:

(A) at least one cyclopentadienyl complex of a transition metal having formula (I):

$$(R)M(R^1)(R^2)(R^3) \qquad (I)$$

wherein:
M is selected from titanium, zirconium and hafnium;
R is an anion containing an η$^5$-cyclopentadienyl ring co-ordinated to M; and
each R$^1$, R$^2$ or R$^3$, independently, represents an organic or inorganic group of an anionic nature σ-bound to M;
the above compound (I) being solid, supported or dispersed in an inert liquid medium; and are the same as each other and are selected from the group consisting of aliphatic carboxylates and fluorocarboxylates.

8. The composition according to claim 1, wherein said component (A) is obtained by putting a complex having formula (I) according to claim 1, wherein R$^1$, R$^2$ and R$^3$ are all different from alkyl or aryl, in contact with a lithium alkyl or a lithium aryl, in such proportions that the atomic ratio Li/M is between 1 and 8, preferably between 1.5 and 4, at a temperature not higher than 100° C., for a period ranging from 5 to 30 minutes.

9. The composition according to claim 8, wherein said organic compound of lithium is selected from the group consisting of lithium methyl, lithium phenyl, lithium benzyl, and the corresponding compounds in which the phenyl ring is substituted by C$_1$–C$_6$ aliphatic groups.

10. The composition according to claim 1, wherein the molar ratio (Mg/M) between the magnesium compound having formula (II) and the compound having formula (I) is between 1:1 and 20:1.

11. The composition according to claim 10, wherein the metal M in the compound having formula (I) is titanium and the molar ratio (Mg/Ti) is between 2:1 and 10:1.

12. A process for the preparation of the catalytic composition according to claim 1, comprising putting the following components (A) and (B) in contact with each other and reacting, in an inert liquid medium, at a temperature ranging from 0° C. to 100° C.:

(A) at least one cyclopentadienyl complex of a transition metal having formula (I):

wherein:

M is selected from titanium, zirconium and hafnium;

R is an anion containing an $\eta^5$-cyclopentadienyl ring co-ordinated to M; and each $R^1$, $R^2$ or $R^3$, independently, represents an organic or inorganic group of an anionic nature σ-bound to M;

the above compound (I) being solid, supported or dispersed in an inert liquid medium; and (B) at least one organometallic compound of magnesium having the following formula (II):

wherein:

$R^4$ is an aliphatic or aromatic hydrocarbon group having from 1 to 20 carbon atoms, $R^5$ is halogen or a group such as $R^4$, and "n" is a decimal number between 0.5 and 2.0.

13. The process according to claim 12, wherein the proportions between components (A) and (B) are such that the ratio between Mg and M is between 1 and 20.

14. The process according to claim 12 or 13, wherein the inert liquid medium is selected from the group consisting of aliphatic or cycloaliphatic saturated hydrocarbons having from 3 to 15 carbon atoms and relative mixtures.

15. The process according to claim 12, wherein said components (A) and (B) are reacted in the presence of an optional modifier (C) consisting of a polar aprotic organic compound.

16. The process according to claim 15, wherein said modifier (C) is selected from the group consisting of organic ethers and polyethers having from 2 to 30 carbon atoms.

17. The process according to claim 15 or 16, wherein the modifier (C) is selected from the group consisting of cyclic ethers and di- or poly-$C_1$–$C_4$-alkylethers of ethylene glycol and diethyleneglycol.

18. The process according to claim 15, wherein the molar ratio between the metal M and the modifier (C) is between 0.003 and 100.

19. The process according to claim 15, wherein the modifier (C) is added in a mixture with component (A), and the reaction between component (B) and the mixture of (A) and (C) takes place at a temperature ranging from 20 to 70° C.

20. The process according to claim 19, wherein component (A) is obtained by the reaction between a compound having formula (I) with M=Ti, and a lithium alkyl or aryl, and the modifier (C) is introduced into the catalytic composition in a mixture with the lithium compound.

21. The process according to claim 15, wherein components (A), (B) and optionally (C), are put in contact and reacted in an inert diluent which is the solvent for the subsequent hydrogenation process.

22. The process according to claim 15, wherein components (A), (B) and optionally (C) are put in contact and reacted in the presence of hydrogen.

23. The process according to claim 15, wherein components (A), (B) and optionally (C) are put in contact and reacted in the presence of an olefinically unsaturated substrate.

24. The process according to claim 15, wherein said composition is not isolated but used directly in the presence of the reaction diluent.

25. The process according to claim 15, wherein components (A), (B) and optionally (C) are put in contact and reacted in the presence of an aromatic hydrocarbon.

26. A process for the selective hydrogenation of olefinic double bonds of a monomeric or polymeric, olefinically unsaturated substrate, comprising putting in contact and reacting said substrate with hydrogen, in an inert solvent, under suitable conditions of pressure and temperature, in the presence of the catalytic composition according to claim 1 for a period which is sufficient to have a selective hydrogenation of at least 50% of the olefinic double bonds.

27. The process according to claim 26, wherein said substrate consists of aliphatic and aromatic olefins having from 2 to 30 carbon atoms, esters of unsaturated carboxylic acids, vinyl esters of aliphatic or aromatic acids, organic imines.

28. The process according to claim 26, wherein the substrate consists of a copolymer of a vinylaromatic compound with a conjugated diene.

29. The process according to claim 28, wherein the vinylaromatic compound is styrene and the conjugated diene is selected from the group consisting of butadiene and isoprene.

30. The process according to claim 26, wherein the hydrogenation is conducted under a hydrogen pressure ranging from 0.5 to 10 MPa and at temperatures ranging from 40 to 110° C., on non-polymeric substrates, and at temperatures ranging from 20 to 150° C. and hydrogen pressures ranging from 0.1 to 10 MPa, on polymeric substrates.

31. The process according to claim 30, wherein the polymeric substrate is in solution in a solvent selected from aliphatic or cycloaliphatic saturated hydrocarbons having from 6 to 15 carbon atoms, and relative mixtures.

32. The composition according to claim 1, wherein element M is titanium.

33. The composition according to claim 12, wherein element M is titanium.

* * * * *